(12) United States Patent
Ishikura (10) Patent No.: US 6,190,012 B1
(45) Date of Patent: Feb. 20, 2001

(54) CORNEA SHAPE MEASURING APPARATUS (75) Inventor: Yasuhisa Ishikura, Tokyo (JP)

(73) Assignee: Kabushiki Kaisha Topcon, Tokyo (JP)

( * ) Notice: Under 35 U.S.C. 154(b), the term of this patent shall be extended for 0 days.

(21) Appl. No.: 09/560,568

(22) Filed: Apr. 28, 2000

(30) Foreign Application Priority Data

Apr. 28, 1999 (JP) .................................................. 11-122287

(51) Int. Cl.⁷ ....................................................... A61B 3/10
(52) U.S. Cl. ............................................................ 351/212
(58) Field of Search ................................... 351/211, 212, 351/214, 221; 600/405, 473, 558, 476; 606/4, 5

(56) References Cited

U.S. PATENT DOCUMENTS 5,307,096 * 4/1994 Baroth et al. ......................... 351/212
5,873,832 * 2/1999 Maloney et al. ...................... 600/473

* cited by examiner

Primary Examiner—George Manuel
(74) Attorney, Agent, or Firm—Oblon, Spivak, McClelland, Maier & Neustadt, P.C.

(57) ABSTRACT

To provide a cornea shape measuring apparatus which is possible, without making the entire apparatus larger-scaled, to increase the number of transparent ring-shaped patterns and project the ring-shaped patterns over the wide range of the cornea of the subject's eye, and the distance between the outermost transparent ring-shaped pattern and the cornea of the subject's eye is made substantially the same as the distance between the inner transparent ring-shaped pattern and the cornea of the subject's eye to enable obtainment of sufficient illuminating quantity of light with a minimum light source. The cornea shape measuring apparatus in which concentric ring-shaped pattern light which is emitted from a plurality of ring-shaped light sources and passed through a plurality of transparent ring-shaped patterns is projected as ring-shaped images on the cornea of the subject's eye, wherein an outer transparent ring-shaped pattern for making a part of light emitted from the outermost ring-shaped light source a ring-shaped pattern, and a ring-shaped refractive prism reflected toward the subject's eye or a ring-shaped reflecting plate is provided along the outer peripheral edge of a pattern plate.

2 Claims, 9 Drawing Sheets

CORNEA SHAPE MEASURING APPARATUS

BACKGROUND OF THE INVENTION

1. Field of the Invention

The present invention relates to a cornea shape measuring apparatus capable of measuring an eye's refractive index and a shape of the cornea of the subject's eye.

2. Description of the Prior Art

As a cornea shape measuring apparatus for measuring a cornea shape precisely, there has been heretofore known a cornea shape measuring apparatus comprising a planar and circular pattern plate, a concentric circle shape light transparent portion, namely, a transparent ring-shaped pattern (a placido pattern) provided on the pattern plate, and a light source disposed behind the pattern plate, the light emitted from the light source being formed into light flux of a number of concentric circle shape ring-shaped patterns through the transparent ring-shaped pattern, the light flux of the concentric circle shape ring-shaped patterns being projected toward the cornea of the subject's eye, to what degree the concentric circle shape transparent pattern changes as compared with the projected pattern shape being recognized so that the shape of the cornea is judged from the obtained change in shape.

In such a cornea shape measuring apparatus as described above, in case of obtaining the cornea shape accurately, it is suggested that the number of concentric circle shape transparent ring-shaped patterns be as many as possible. However, if an attempt is made to increase the number of transparent ring-shaped patterns, the outermost pattern out of the ring-shaped patterns provided on the pattern plate is enlarged in its diameter, thus the entire apparatus being large-sized. Thus there is a limit in increasing the number of transparent ring-shaped patterns.

Further, where an attempt is made to increase the number of transparent ring-shaped patterns, there arises a problem in that since the pattern plate is away from the subject's eye, a large quantity of light is necessary for the light source. Particularly, outer one of the transparent ring-shaped patterns of the pattern plate is away from the subject's eye, hence the quantity of light projected from the outer transparent ring-shaped pattern lowers. Therefore, in order that the quantity of light of the ring-shaped patterns projected on the subject's eye from a number of transparent ring-shaped patterns is made substantially uniform, it is necessary to make the quantity of light from the outer transparent ring-shaped patterns larger.

It is therefore an object of the present invention to provide a cornea shape measuring apparatus capable of increasing the number of transparent ring-shaped patterns, without making the entire apparatus large-sized, to project the ring-shaped patterns over a wide range of the cornea of the subject's eye, and obtaining a sufficient quantity of illuminating light with the minimum light source.

SUMMARY OF THE INVENTION

For achieving the aforementioned primary object, in accordance with a first aspect of the present invention, there is provided a cornea shape measuring apparatus comprising:

- a pattern plate having a plurality of transparent ring-shaped patterns which is different in diameter with a plurality of masking portions therebetween;
- a plurality of ring-shaped light sources which are disposed behind and adjacent to the pattern plate and arranged in concentric circle shape along the plurality of transparent ring-shaped patterns, thereby concentric circle pattern light as a placido pattern being projected on the cornea of the subject's eye;
- an outer transparent ring-shaped pattern plate for making ring-shaped light out of part of the light projected from some of the plurality of light sources disposed at most exterior positions; and
- a ring-shaped reflecting member disposed along the outer edge of the pattern plate in order to reflect the light from the outer transparent ring-shaped pattern plate.

In accordance with a second aspect of the present invention, the ring-shaped reflecting member comprises a ring-shaped refractive prism or a ring-shaped reflecting plate.

BRIEF DESCRIPTION OF THE DRAWINGS

The present invention will now be further illustrated in the following non-limiting specific embodiments with reference to the annexed drawings, in which.

DESCRIPTION OF THE PREFERRED EMBODIMENT

The embodiment of a cornea shape measuring apparatus for measuring a cornea shape by projecting a placido pattern according to the present invention will be described hereinafter with reference to the drawings.

Figure 4A:
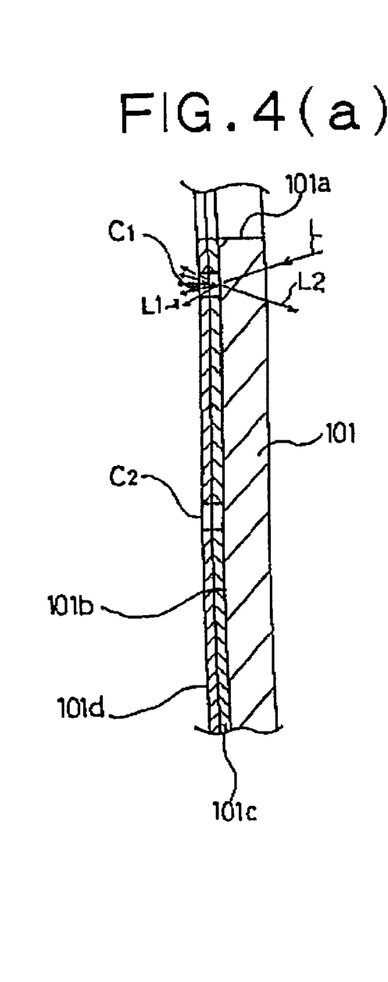
FIG. 4A is an enlarged sectional view showing a part of the constitution of the pattern plate shown in FIG. 3.
Figures 4B, 4C:
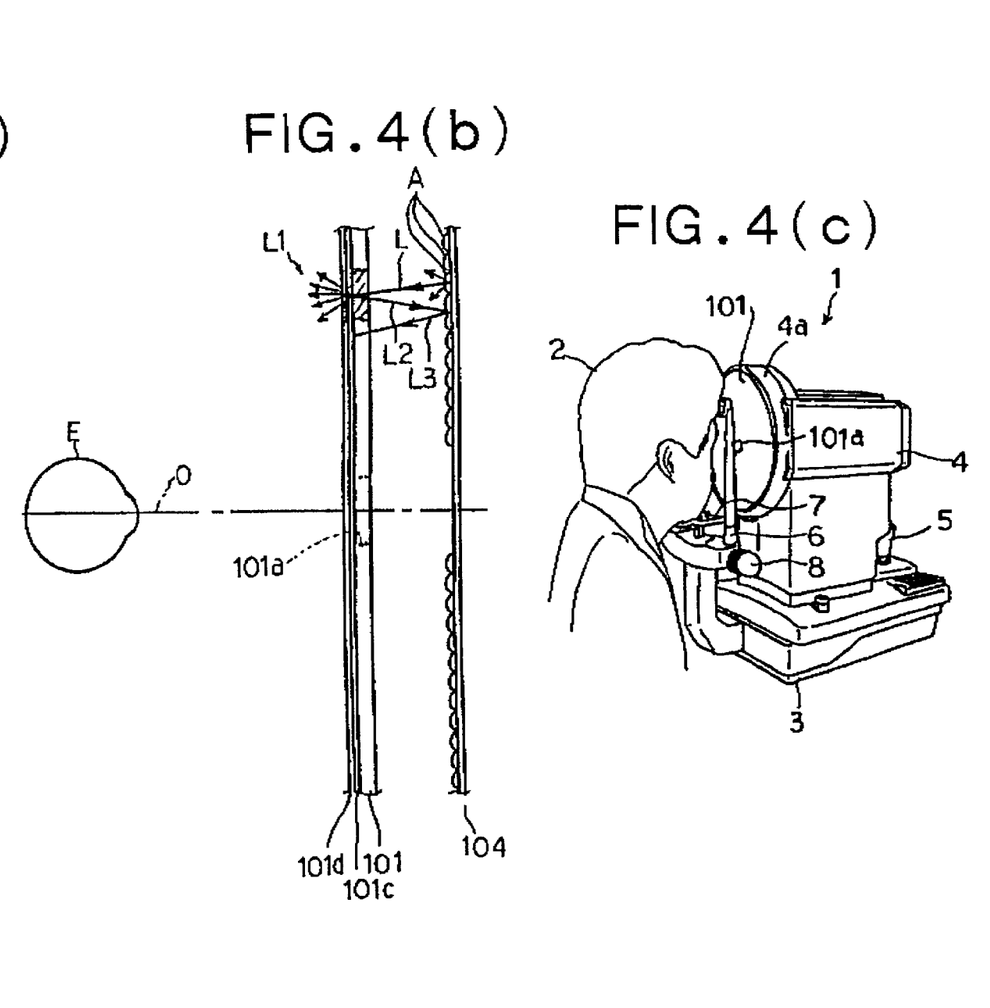
FIG. 4B is an explanatory view showing a relationship between a pattern plate and a PC plate.
FIG. 4C is a perspective view showing a relationship between the cornea shape measuring apparatus according to the present invention and the subject's person.

FIG. 4C shows a relationship between the cornea shape measuring apparatus 1 according to the present invention and the subject 2. The cornea shape measuring apparatus 1 comprises a base 3, an apparatus body 4 mounted on the base 3 in a manner capable of being moved back and forth and left and right, a joy-stick 5 mounted on the apparatus body 4 to control the movement of back and forth and left and right of the apparatus body 4, a frame 6 mounted on the front end of the base 3, a chin rest 7 provided on the frame 6 movably up and down, and an operating knob 8 held on the frame 6 to operate the vertical movement of the chin rest 7.

Figure 1:
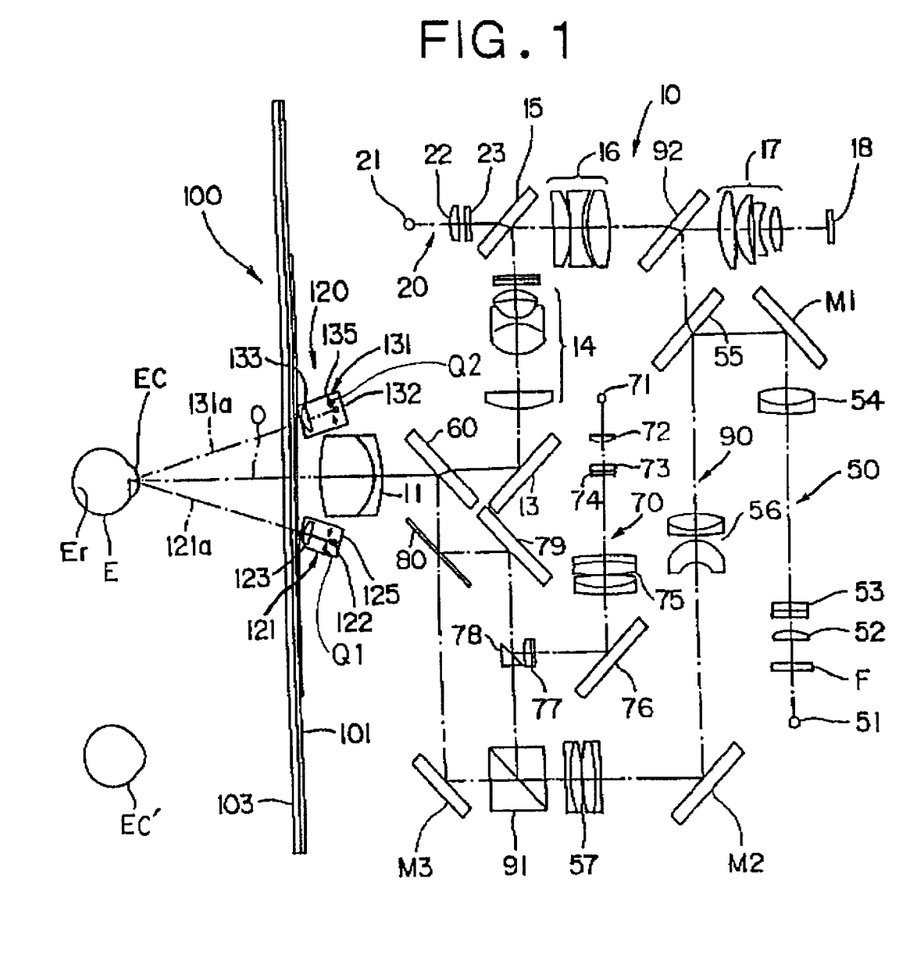
FIG. 1 is an optical arranging view showing the arrangement of an optical system of a cornea shape measuring apparatus according to the present invention.

The apparatus body 1 comprises, as shown in FIG. 1, a front eye portion observing optical system 10 for observing the front eye portion of the subject's eye E, a gaze fixing index projecting optical system 50 for projecting a gaze fixing index on the subject's eye E, a measurement projecting optical system 70 for projecting a measuring light for measuring an eye refractive index on the fundus Er of the subject's eye E, a light receiving optical system 90 for receiving a measurement light reflected at the fundus Er, a placido pattern projecting system 100 for projecting a plachido pattern for measuring a cornea shape on the cornea Ec of the subject's eye E, and a mark projecting optical system 120 for projecting an operation distance detecting mark on the cornea Ec.

The front eye portion observing optical system 10 comprises an objective lens 11, a dichroic mirror 60, a mirror 13, a relay lens 14, a dichroic mirror 15, a relay lens 16, a focusing lens 17, and an area sensor (a two-dimensional image pickup element) 18 composed of CCD as a light receiving means.

The front eye portion observing optical system 10 has a scale projecting system 20 for forming a cross-shaped scale image P (see FIG. 7) provided on the area sensor 18. The scale projecting system 20 comprises a light source 21, a condenser lens 22, and a scale plate 23 formed with a scale (not shown), wherein light emitted from the light source 21 is condensed in the condenser lens 22 to irradiate the scale plate 23, whereby the cross-shaped light reaches the focusing lens 17 through the dichroic mirrors 15 and 92 from the scale plate 23, and a scale image P is formed on the area sensor 18 by the focusing lens 17. This scale image P along with the front eye portion is displayed on a monitor 202 (see FIG. 7).

The gaze fixing index projecting optical system 50 comprises a light source 51, a filter F for cutting infrared rays, a condenser lens 52, a gaze fixing index plate 53, a relay lens 54, a mirror M1, a dichroic mirror 55, a relay lens 56, a mirror M2, a relay lens 57, a mirror M3, a dichroic mirror 60, and an objective lens 11. The gaze fixing index plate 53 is in a position in conjugation with the fundus Er, the gaze fixing index plate 53 being formed with a mark (not shown) serving as a gaze fixing index, which mark is projected on the fundus Er. The projection of the mark causes the subject's eye E to be directed in a fixed direction.

The measurement projecting optical system 70 comprises a light source 71, a condenser lens 72, a conical prism 73, a ring opening plate 74 formed with a ring opening (not shown), a relay lens 75, a mirror 76, a relay lens 77, a dichroic mirror 78, a mirror 79, a dichroic mirror 80, a dichoric mirror 60, and an objective lens 11.

The conical prism 73 is provided to condense light from the light source 71 condensed by the condenser lens 72 in the ring opening of the ring opening plate 74. The ring opening plate 74 and the fundus Er are in a conjugation opposition, and a ring image (not shown) is projected on the fundus Er by the light passing through the ring opening of the ring opening plate 74.

The reflecting light of the ring image projected on the fundus Er is focused on the area sensor 18 through the objective lens 11, the dichroic mirror 60, the dichroic mirror 80, the mirror 79, the dichroic mirror 78, the dichroic mirror 91, the relay lens 57, the mirror M2, the relay lens 56, the dichroic mirror 55, the dichroic mirror 92, and the focusing lens 17 to form an ring image. The eye refractive index is obtained from the ring image by operation through an arithmetic control device 203 which will be mentioned later.

The light receiving optical system 90 is composed of an objective lens 11, a dichroic mirror 60, a dichroic mirror 80, a mirror 79, dichroic mirrors 78, 91, a relay lens 57, a mirror M2, a relay lens 56, dichroic mirrors 55, 92, a focusing lens 17, and an area sensor 18.

Figure 2:
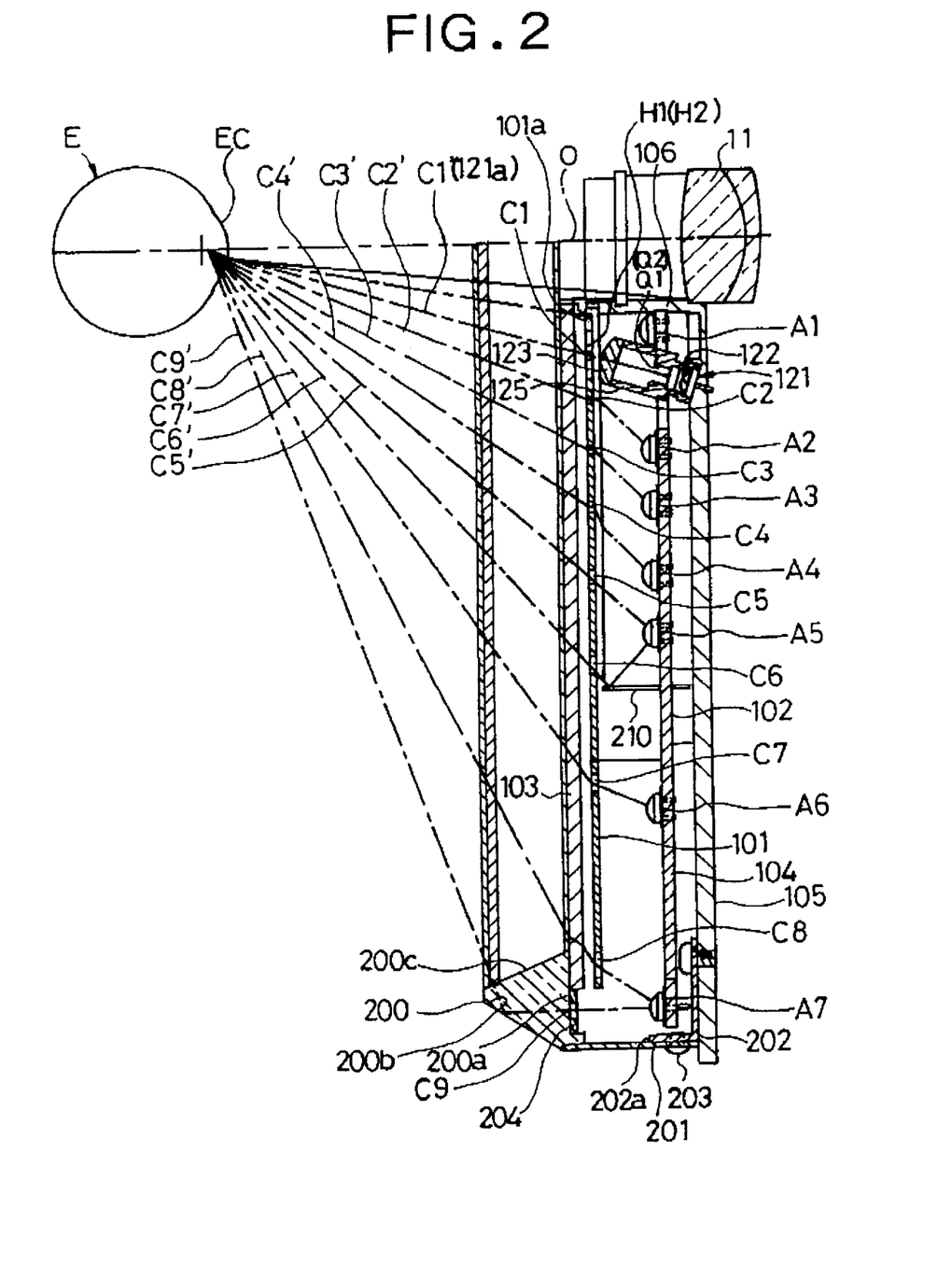
FIG. 2 is a sectional view showing the constitution of a placido pattern projecting system.

As shown in FIG. 2, the placido pattern projecting system 100 is composed of a placido pattern plate 101, a light source portion 102, a visible light cut filter 103, and a refractive prism 200.

Figure 3:
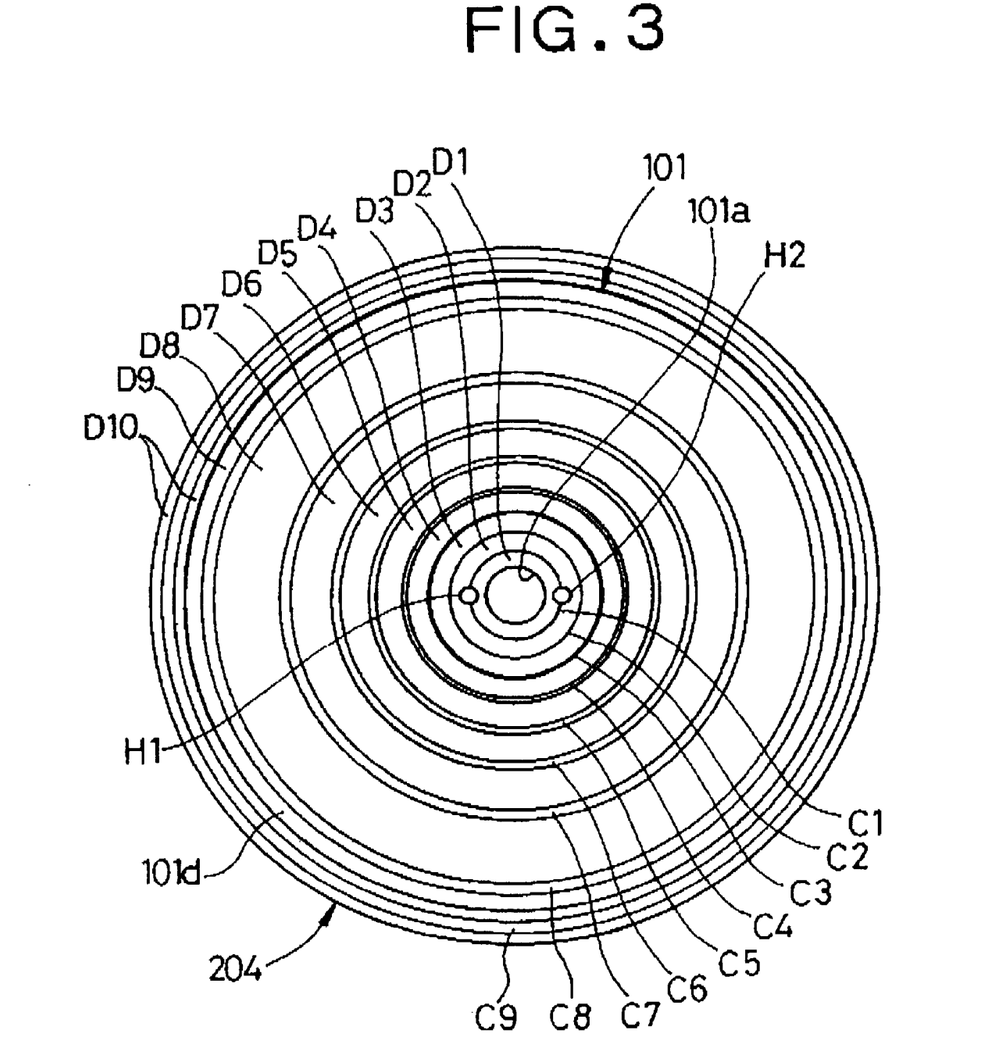
FIG. 3 is a front view showing two pattern plates of the placido pattern projecting system shown in FIG. 2.

The base of the pattern plate 101 comprises a diffusion plate capable of transmitting and diffusing light. As shown in FIG. 3, the pattern plate 101 is bored at its center with a circular hole 101a, and is formed with eight transparent ring-shaped patterns C1–C8 which are concentric circular provided concentrically around the hole 101a and through which light transmits. In the outer circumference of the pattern plate 101 is arranged a narrow ring-shaped pattern plate 204. The pattern plate 204 is formed with an outer transparent ring-shaped pattern C9 which is concentric with the rings C1–C8 and through which light can be transmitted.

As shown in FIG. 3, the rings C1–C8 are formed on the surface 101b of the pattern plate 101a, by forming on the surface 101b a plurality of masking portions D1–D9. The masking portions D1–D9 comprise a white coating layer 101c (a white reflecting layer) and a black coating layer 101d (a black layer) in a concentrically spaced relation. The rings C1–C8 are formed between those masking portions D1–D9.

Further, as shown in FIG. 3, the ring C9 is formed, by forming masking portions D10, D10 on the surface of the pattern plate 204 in concentrically spaced relation. Thus the ring C9 is formed between the masking portions D10, D10. Similarly, the masking portions D10 is also formed to the masking portions D1–D9.

The pattern plate 101 is formed with two circular holes H1 and H2 lined in a horizontal direction. Similar to the above, the holes H1 and H2 are not applied with the coatings 101c and 101d. The holes H1 and H2 are provided to cause the light from a mark projecting optical system 120 described later to pass through.

The light source portion 102 comprises a number of infrared light emitting diodes A mounted on the disk-shaped PC plate 104. The infrared light emitting diodes A are arranged along the transparent ring-shaped pattern C, namely, on the concentric circle with an optical axis O as the center figure (see FIG. 5).

Figure 5:
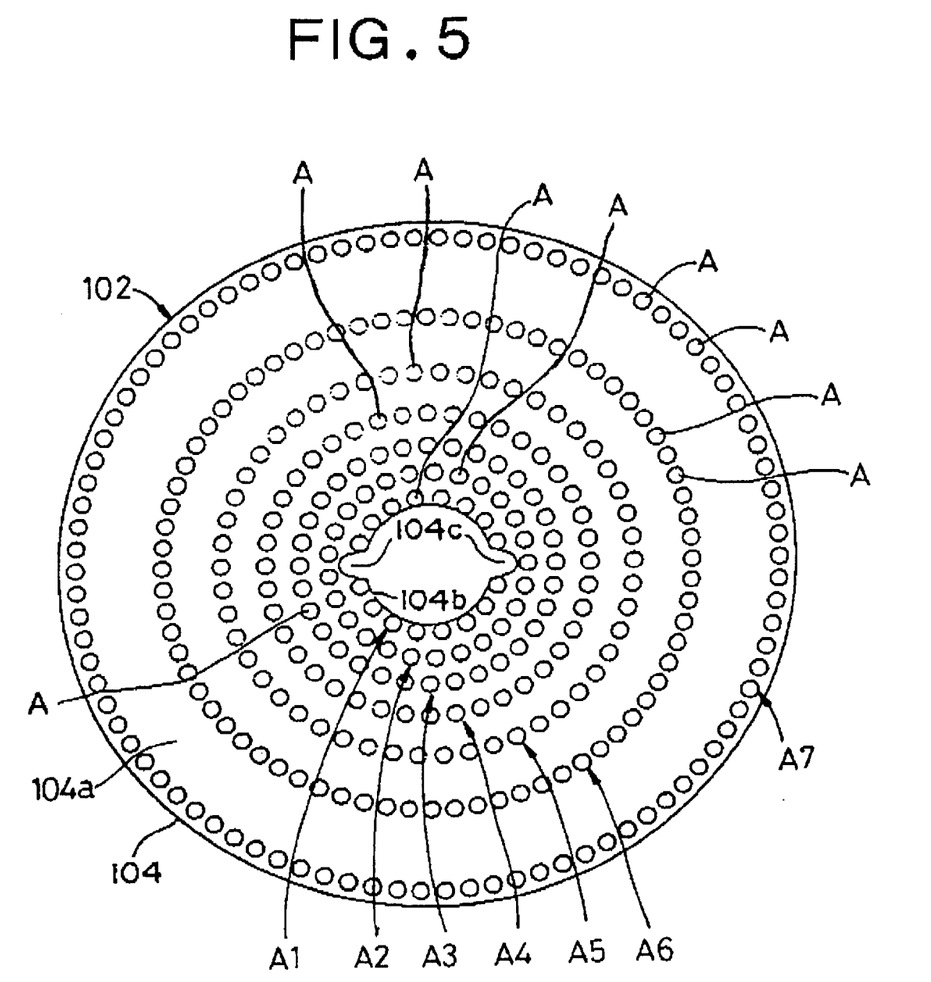
FIG. 5 is a front view of a PC plate showing the arrangement of infrared light emitting diodes.

Thereby, a number of light emitting diodes A constitute a plurality of concentric ring-shaped light sources A1–A7. The PC plate 104 is mounted on the unit base 105.

Even if the placido pattern of the pattern plate 101 is projected on the subject's eye by the infrared light emitting diodes A, the placido pattern is free from calling the subject's eye's attention because the former is projected by infrared rays.

A white reflecting layer (not shown in the figure) is provided on the surface of the PC plate 104 on which the infrared light emitting diodes A are provided (the surface on the side opposite to the pattern plate 101). This reflecting layer can be formed handily by applying a white coating on the PC plate 104 using a printing means for carrying out white silk printing.

Further, on the PC plate 104 is provided a tubular reflecting plate 210 disposed concentrically on the outer circumference of the ring-shaped light source A5.

The unit base 105 is provided integral with a lens tube portion 106 which holds the objective lens 11.

It is noted that the visible light cut filter 103 may be substituted by a filter of low visible light transmittance. An anti-reflection coating layer 103a is applied to the surface on the subject's eye E side of the visible light cut filter 103. Moreover, the visible light cut filter 103 is disposed between the subject's eye E and the pattern plate 101 to prevent the placido pattern of the pattern plate 101 from being viewed by the subject 2. The anti-reflection coating layer 103a serves to prevent the image of subject 2 himself (or herself) from being reflected in the visible light cut filter 103 and viewed by the subject 2.

Thereby, in the eye refraction measurement, the placido pattern or the image of the subject's person attracts no attention of the subject's eye preventing from the adjusting action of the subject's eye, and enabling the accurate eye refraction measurement.

Further, a bracket 202 having an L-shape in section is secured to the peripheral edge of the unit base 105, and a tubular-shaped (ring-shaped) mounting plate 201 is secured to an erected portion 202a of the bracket 202 by means of a screw 203. A ring-shaped refractive prism (ring-shaped reflecting means) 200 having a substantially triangular shape in section is fitted in and secured to the mounting plate 201. Thereby, the refractive prism 200 is disposed concentric with the transparent ring-shaped patterns C1–C9 on the outer peripheral edge of the visible light cut filter 103.

The refractive prism 200 is fixedly mounted on the front surface of the peripheral edge of the visible light cut filter 103 in the bottom 200a. The refractive prism 200 has an outer light reflecting surface 200b inclined inwardly from the outside periphery with respect to the bottom 200a, and a light outgoing surface 200c inclined from the inner periphery of the bottom 200a to the outside. Further, a ring-shaped pattern plate 204 fixedly mounted on the bottom 200a is fitted in and adhesively secured to the outer peripheral surface of the visible light cut filter 103. The front surface of the visible light cut filter 103 and the front surface of the pattern plate 204 are provided on a substantially one plane. The light outgoing surface 200c is applied with a visible light cut coating (not shown).

The mark projecting optical system 120 is composed of a pair of parallel projecting units 121 and 131 (see FIG. 1) disposed in the same plane. The parallel projecting unit 121 comprises an infrared light emitting diode 122, a pin hole Q1, a projecting lens 123 for emitting the infrared light emitted from the pin hole Q1 toward the holes H1 and H2 in the form of parallel light, and lens tubes 125 and 135 for holding the former. The parallel projecting unit 131 comprises an infrared light emitting diode 132, a pin hole Q2, a projecting lens 133 for emitting infrared light emitted from the pin hole Q2 toward the holes H1 and H2 in the form of parallel light, and lens tubes 126 and 135 for holding the former.

Optical axes 121a and 131a of the parallel projecting units 121 and 131 are directed at the cornea Ec of the subject's eye passing through the holes H1 and H2. The parallel light caused by the projecting lenses 123 and 133 are projected toward the cornea Ec of the subject's eye.

A case 125 of the parallel projecting unit 121 is inserted into a recess 104c of a hole 104b formed in the center of the PC plate 104, and is secured to the unit base 105. The parallel projecting unit 131 is also secured to the unit base 105 similarly to the parallel unit 121.

Figure 6:
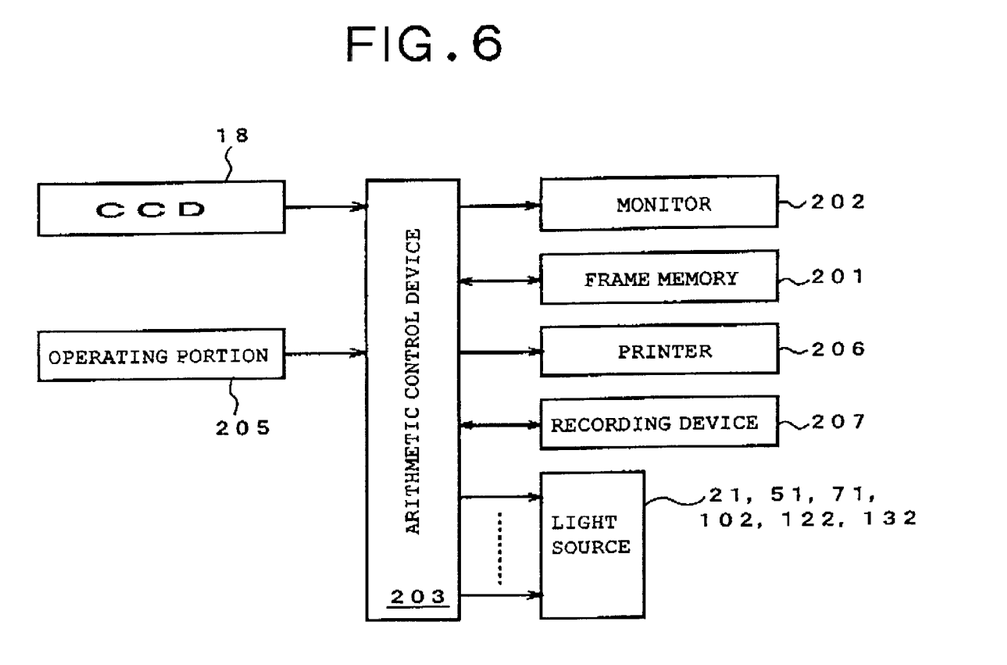
FIG. 6 is a block diagram showing the constitution of a control system of the cornea shape measuring apparatus.

FIG. 6 is a block diagram showing the constitution of a control system of the cornea shape measuring apparatus. In FIG. 6, reference numeral 201 designates a frame memory for storing an image received by an area sensor 18; 202 is a monitor displaying the image received by the area sensor 18;

and 203 is an arithmetic control device for operating and obtaining a cornea shape from ring images Ca–Ci (see FIG. 7) of images stored in the frame memory 201, detecting the working distance of the apparatus body based on the ratio between the diameter L1 of the ring image Cb and the distance L2 between reflecting images Qa and Qb, and correcting the cornea shape on the basis of the operating distance. The arithmetic control device 203 has functions as the cornea shape operating means, the operating distance detecting means, and the correcting means.

The placido pattern projecting system 100, the mark projecting optical system 120, the front eye portion observing optical system 10, and the arithmetic control device 203 constitute the cornea shape measuring apparatus for measuring a shape of the cornea.

The arithmetic control device 203 controls a printer 206, a recording device 207, light sources 21, 51, 71, 102, 122, 132, etc. on the basis of the operation of the operating portion 205. The arithmetic control device 203 is provided to calculate the eye refractive index from the ring image projected on the fundus Er.

The operation of the aforementioned embodiment will be explained hereinafter. The infrared light emitting diodes A of the placido pattern projecting system 100 and the infrared light emitting diodes 122 and 132 of the mark projecting optical system 120 are turned on by the operation of the operating portion 206. Also, the light source 21 of the scale projecting system 20 is turned on.

In this state, the light sources 102 of the ring-shaped light sources A1–A7 are turned on. Thereby, a part of light directed at the rings C1–C9 out of light from a plurality of infrared light emitting diodes A repeats diffusion and reflection as shown at L, L1, and L2 in FIGS. 4A and 4B by the action of the masking portions D1–D 10 and the PC plates 104 and 204.

Namely, the action of diffusion and reflection will be explained using the ring C1 and one infrared light emitting diode A. The greater part of the light L emitted from the infrared light emitting diode and directed to the transparent ring-shaped pattern C1 passes through, the ring-shaped pattern C1 as the diffusion light L1 and the hole 101a, while the remainder thereof reflects as the reflection light L2 on the PC plate 104. The reflecting light L2 and the light directly turned toward the masking portions D1–D10 from the infrared light emitting diodes A are reflected as the reflecting light L3 at the PC plate 104, and they are reflected many times between the portion of the white coating layer (white reflecting layer) 101c and the PC plate 104 and thereafter projected on the subject's eye E side from one of the rings C1–C9. Thereby, the light emitted from the infrared light emitting diodes A is utilized without waste for the purpose of projecting the placido ring-shaped patterns, and can project the illuminating light on the placido patterns uniformly.

While in the present embodiment, the pattern plate 101 is formed from a diffusion plate, the pattern plate is not always limited thereto. For example, a pattern plate and a diffusion plate (not shown) are formed separately and lay one on top of another, and the aforementioned masking portions D1–D10 may be formed between the pattern plate and the diffusion plate.

On the other hand, by turning on the infrared light emitting diodes A of the ring-shaped light sources A1–A4, a part of the light emitted from the ring-shaped light sources A1–A4 is directly projected on the cornea Ec of the subject's eye through the transparent ring-shaped patterns C1–C4 and the visible light cut filter 103 as indicated at C1'–C4' in FIG. 2.

Further, by turning on the infrared light emitting diodes A of the ring-shaped light source A5, a part of the light emitted from the ring-shaped light source A5 is directly projected on the cornea Ec of the subject's eye through the transparent ring-shaped pattern C5 and the visible light cut filter 103 as indicated at C5' in FIG. 2. On the other hand, a part of the remainder of the light emitted from the ring-shaped light source A5 is reflected at the tubular reflecting plate 210 as indicated at C6' in FIG. 2, and thereafter is projected on the cornea Ec of the subject's eye through a transparent ring-shaped pattern C6 described later and the visible light cut filter 103.

Further, by turning on the infrared light emitting diodes A of the ring-shaped light source A6, a part of the light emitted from the ring-shaped light source A6 is directly projected on the cornea Ec of the subject's eye through the transparent ring-shaped pattern C7 and the visible light cut filter 103 as indicated at C7' in FIG. 2.

A part of the light emitted from the ring-shaped light source A7 is directly projected on the cornea Ec of the subject's eye through the transparent ring-shaped pattern C8 and the visible light cut filter 103 as indicated at C8' in FIG. 2. On the other hand, a part of the remainder of the light emitted from the ring-shaped light source A7 passes through the transparent ring-shaped pattern C9 as indicated at C9' in FIG. 2, and is reflected at the reflecting surface 200b of the refractive prism 200, and thereafter is projected on the cornea Ec of the subject's eye from the light emitting surface 200c of the refractive prism 200.

In this manner, the ring-shaped light C1'–C8' in the form of infrared light are emitted through the ring-shaped patterns C1–C8 of the pattern plate 101 and the visible light cut filter 103, the ring-shaped light C9' in the form of infrared light is emitted through the ring C9 of the pattern plate 204 and the light emitting surface 200c applied with a visible light cut coating, and the ring-shaped light C1'–C9' are projected on the cornea Ec of the subject's eye to form the reflecting images caused by the ring-shaped patterns C1–C9.

In a similar manner, the infrared light emitted from the infrared light emitting diodes 122 and 132 are projected on the cornea Ec of the subject's eye in the form of parallel light formed by the projecting lens.

Figure 7:
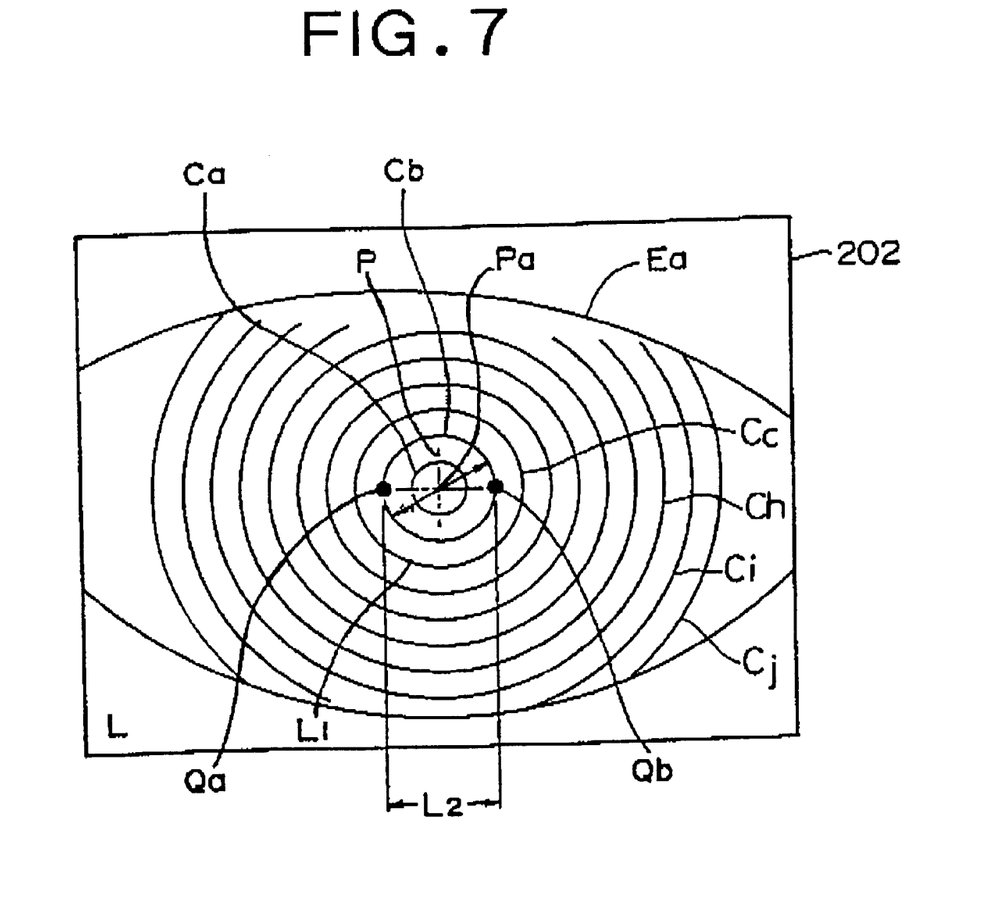
FIG. 7 is an explanatory view showing an image displayed on a monitor.

The light of the ring reflecting image caused by the reflection of the cornea Ec of the subject's eye and of the mark reflecting image are formed on the area sensor 18 together with the front eye portion image through the objective lens 11, the dichroic mirror 60, the mirror 13, the relay lens 14, the dichroic mirror 15, the relay lens 16, the dichroic mirror 92, and focusing lens 17. Reflecting images Ca–Cj and reflecting images Qa and Qb together with a front eye portion image Ea are displayed on the monitor 202 as shown in FIG. 7.

Further, since the scale image is formed on the area sensor 18 by turning on the light source 21 of the scale projecting system 20, the scale image P is also displayed on the monitor 202.

The viewer moves the apparatus body up and down and left and right so that an intersection Pa of the scale image P is positioned at the center of the ring reflecting image Ca while watching the scale image P and the ring reflecting image Ca displayed on the monitor 202 to perform alignment in the XY direction. Further, the viewer moves the apparatus body back and forth so that the reflecting images Qa and Qb substantially coincide with the ring reflecting image Cb to perform alignment in the Z direction.

The mark projecting system 120 projects the parallel light whereby the distance L2 between the mark reflecting images Qa and Qb is constant despite the distance of the apparatus body in the Z direction, while the diameter L1 of the ring reflecting image Cb changes according to distance in the Z direction. Therefore, by comparing the distance L2 with diameter L1, the alignment in the Z direction can be adjusted, and the operating distance can be obtained.

Since the scale image P is displayed on the monitor 202, the alignment can be performed while watching the scale image P, and can be very readily done.

Figure 8:
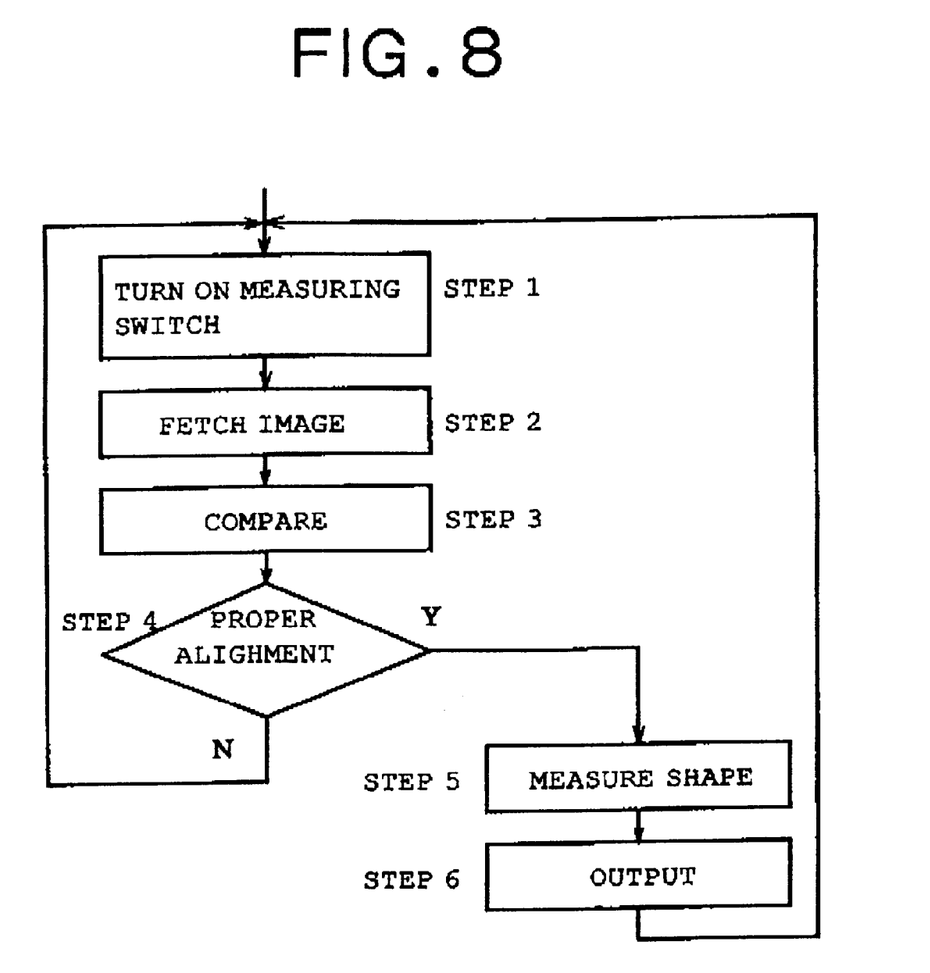
FIG. 8 is a flow chart showing the operation of the cornea shape measuring apparatus.

Upon completion of these alignments, when a measuring switch (not shown) of the operating portion 205 is depressed, in Step 2 shown in FIG. 8, the image shown in FIG. 7 is stored in the frame memory 201.

The arithmetic control portion 203 obtains the ratio between the diameter L1 of the ring reflecting image Cb stored in the frame memory 201 and the distance L2 between the mark reflecting images Qa and Qb to calculate the operating distance of the apparatus body from the resultant ratio. The arithmetic control portion then calculates a difference between the operating distance and the set operating distance preset, namely, an error in alignment in the Z direction (Step 3). Whether or not this error is within a fixed range is judged in Step 4. If yes, the cornea shape is obtained from the ring reflecting images Ca–Cj stored in the frame memory 201, and the cornea shape is corrected according to the error (Step 5). By this correction, even if the alignment in the Z direction is not carried out accurately, the accurate cornea shape is obtained.

The cornea shape before correction, the cornea shape after correction, and the operating distance are displayed on the monitor 202, and these data are printed out by the printer 206 and recorded along with the image shown in FIG. 7 in the recording device 207 (Step 6).

As described above, even if the alignment in the Z direction is not carried out accurately, the error in alignment is obtained, and the cornea shape is corrected on the basis of the error and the accurate cornea shape is obtained. Therefore, even if the operating distance is short, an allowable range of alignment can be set widely, and the accurate cornea shape can be obtained.

Where the eye refractive index is measured, the light source 51 of the gaze fixing index projecting optical system 50 is turned on and the subject's eye E is directed in a fixed direction and viewed cloudy. Then, the light source 71 of the measurement projecting optical system 70 is turned on to project the ring image (not shown) on the fundus E. This ring image is formed in the area sensor 18 through the objective lens 11, the dichroic mirror 60, the dichroic mirror 80, the mirror 79, the dichroic mirror 78, the dichroic mirror 91, the relay lens 57, the mirror M2, the relay lens 56, the dichroic mirror 55, the dichroic mirror 92, and the focusing lens 17, and the arithmetic control device 203 calculates and obtains the eye refractive index from the ring image.

While in the above-described embodiment, the scale image P is also stored in the frame memory 201, it is to be noted that when the measuring switch is depressed, the light source 21 of the scale projecting system 20 is turned off so that the scale image P may not be stored in the frame memory 201. By doing so, when the cornea shape or the operating distance is calculated, the scale image P will not be a hindrance thereto.

Further, while in the above-described embodiment, the pattern plate 204 is mounted on the bottom 200a of the prism 200, it is to be noted that the pattern plate can be mounted on the light omitting surface 200c.

While in the above-described embodiment, when the measuring switch is depressed, the image is fetched in the frame memory 201 to calculate the cornea shape or the operating distance, it is to be noted that the image is always fetched in without depressing the measuring switch, and the operating distance is calculated; and when the operating distance is in a proper range, the cornea shape can be calculated and output.

Modifications will be described below.

Figure 9:
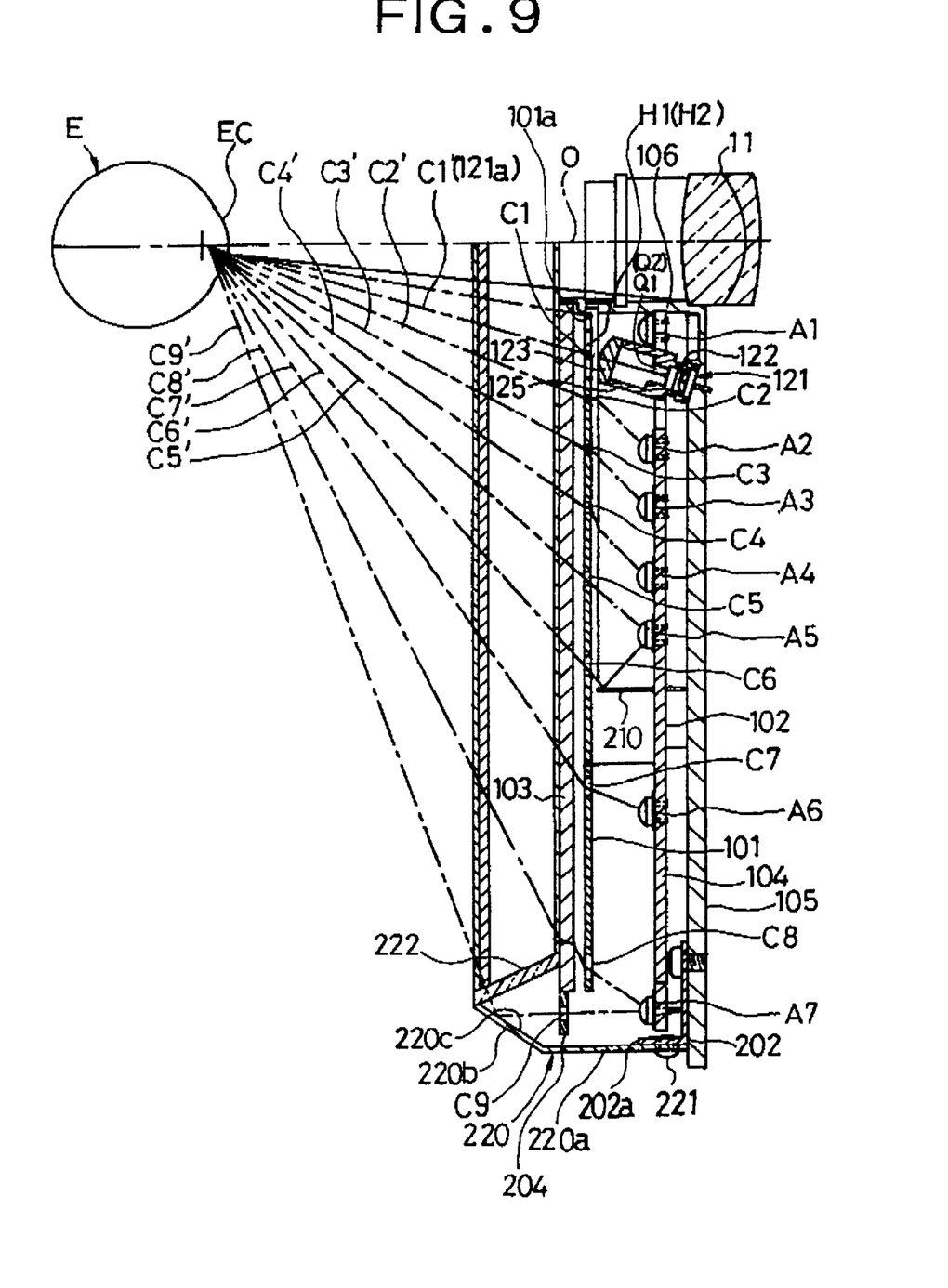
FIG. 9 is an explanatory view of an optical system showing a modified embodiment of the cornea shape measuring apparatus.

While in the aforementioned embodiment, an example has been illustrated in which the ring-shaped refractive prism 200 is used as the ring-shaped reflecting means, which is provided along the peripheral edge of the disk-shaped pattern plate 101, the constitution is not always limited thereto. For example, the constitution as shown in FIG. 9 can be employed. In FIG. 9, a ring plate-shaped pattern plate 204 is fixedly mounted on the outer peripheral surface of the visible light cut filter 103, and a bracket 202 having an L-shape in section is secured to the peripheral edge of the unit base 105. Further, a tubular portion 220a of a ring-shaped reflecting plate (or ring-shaped reflecting means) 220 is secured to an erecting portion 202a of the bracket 202 through a screw 221. Further, the ring-shaped reflecting plate 220 is formed at its extreme end with a conical tubular portion 220b inclined convergently inwardly, and a ring-shaped reflecting surface 220c is formed on the inner surface of the conical tubular portion 220b. Moreover, a visible light cut filter 222 inclined externally so that the diameter thereof is enlarged gradually toward the extreme end is interposed between the inner end of the conical tubular portion 220b and the visible light cut filter 103. The visible light cut filter 222 is fixedly mounted on the peripheral edge of the visible light cut filter 103.

A part of light emitted from the ring-shaped light source A7 is projected on the cornea Ec of the subject's eye directly through the transparent ring-shape pattern C8 and the visible light cut filter 103. Further, a part of the reminder of light emitted from the ring-shaped light source A7 passes through the transparent ring-shaped pattern C9, after which it is reflected at the reflecting surface 220c of the tubular reflecting plate 220, and thereafter is projected on the cornea Ec of the subject's eye through the visible light cut filter 222.

It is noted that since other constitutions and operations are similar to those mentioned in the embodiments shown in FIGS. 1 to 8, description of which is omitted.

As described above, in accordance with the first aspect of the present invention there is provided a cornea shape measuring apparatus comprising: a pattern plate having a plurality of transparent ring-shaped patterns which is different in diameter with a plurality of masking portions therebetween; a plurality of ring-shaped light sources which are disposed behind and adjacent to the pattern plate and arranged in concentric circle shape along the plurality of transparent ring-shaped patterns, thereby concentric circle pattern light as a placido pattern being projected on the cornea of the subject's eye; an outer transparent ring-shaped pattern plate for making ring-shaped light out of part of the light projected from some of the plurality of light sources disposed at most exterior positions; and a ring-shaped reflecting member disposed along the outer edge of the pattern plate in order to reflect the light from the outer transparent ring-shaped pattern plate. With this constitution, it is possible, without making the entire apparatus larger-scaled, to increase the number of transparent ring-shaped patterns and project the ring-shaped patterns over the wide range of the cornea of the subject's eye, and the distance between the outermost transparent ring-shaped pattern and the cornea of the subject's eye is made substantially the same as the distance between the inner transparent ring-shaped pattern and the cornea of the subject's eye to enable obtainment of sufficient illuminating quantity of light with a minimum light source.

The foregoing is considered illustrative of the principles of the invention. Accordingly, it is contemplated that the scope of the invention as claimed encompass all obvious variation, modification and equivalents which may occur to those skilled in the art.

What is claimed is:

1. A cornea shape measuring apparatus comprising:
   (1) a pattern plate having a plurality of transparent ring-shaped patterns which is different in diameter with a plurality of masking portions therebetween;
   (2) a plurality of ring-shaped light sources which are disposed behind and adjacent to the pattern plate and arranged in concentric circle shape along said plurality of transparent ring-shaped patterns, thereby concentric circle pattern light as a placido pattern being projected on the cornea of the subject's eye;
   (3) an outer transparent ring-shaped pattern plate for making ring-shaped light out of part of the light projected from some of the plurality of light sources disposed at most exterior positions; and
   (4) a ring-shaped reflecting member disposed along the outer edge of the pattern plate in order to reflect the light from the outer transparent ring-shaped pattern plate.

2. A cornea shape measuring apparatus according to claim 1, wherein said ring-shaped reflecting member comprises a ring-shaped refractive prism or a ring-shaped reflecting plate.

* * * * *